United States Patent [19]

Walsh

[11] Patent Number: 5,210,499

[45] Date of Patent: May 11, 1993

[54] IN-SITU SENSOR METHOD AND DEVICE

[75] Inventor: Shawn M. Walsh, Lowell, Mass.

[73] Assignee: The United States of America as represented by the Secretary of the Army, Washington, D.C.

[21] Appl. No.: 614,656

[22] Filed: Nov. 16, 1990

[51] Int. Cl.⁵ .................. G01N 27/00; G01R 27/02
[52] U.S. Cl. ..................... 324/649; 526/60; 324/724; 324/71.1
[58] Field of Search ............ 324/649, 690, 724, 71.1; 340/604, 605, 632; 526/60

[56] References Cited

U.S. PATENT DOCUMENTS

| | | | |
|---|---|---|---|
| 2,953,764 | 9/1960 | Tellkamp . | |
| 3,349,359 | 10/1967 | Morey . | |
| 3,383,863 | 5/1968 | Berry . | |
| 3,594,557 | 7/1971 | Anderson | 340/632 |
| 3,791,792 | 2/1974 | Lindsay | 324/71.1 |
| 4,352,059 | 9/1982 | Senturia et al. . | |
| 4,423,371 | 12/1983 | Senturia et al. | 324/61 R |
| 4,496,697 | 1/1985 | Zsduay et al. | 526/60 |
| 4,777,431 | 10/1988 | Day et al. . | |
| 4,795,998 | 1/1989 | Dunbar et al. | 338/5 |
| 4,965,554 | 10/1990 | Darling | 340/604 |

OTHER PUBLICATIONS

Hofer, "Fibre Optic Damage Detection in Composite Structures," *Composites*, 18(4), (Sep. 1987).

*Primary Examiner*—Kenneth A. Wieder
*Assistant Examiner*—Maura K. Regan
*Attorney, Agent, or Firm*—Saul Elbaum; Freda L. Krosnick

[57] ABSTRACT

An apparatus and method for accurately monitoring the flow and cure rate of a resin material. The method is accomplished through the use and incorporation of efficient sensors as integral components of a composite resin structure material. The sensors used are electrically conductive threads arranged in a non-intersecting, grid-like configuration. They may be placed into or between composite resin materials. These sensors serve as leads which are connected to a computer through a multiplexer/rapid switching system and a scanner. The data obtained for the monitoring of the flow and cure of resin is stored on a computer system and is presented on the computers' graphic window.

15 Claims, 9 Drawing Sheets

IN-SITU SENSOR METHOD AND DEVICE

GOVERNMENTAL INTEREST

The invention described herein may be manufactured, used and licensed by or for the U.S. Government for governmental purposes without the payment to me of any royalties thereon.

BACKGROUND OF THE INVENTION

The ability to produce a composite material having specified properties is of great importance in a variety of military, as well as commercial fields. Being able to monitor the production of these materials in order to assure the presence of the essential properties required for a specific purpose would be a significant advancement in the composite material art. Monitoring the production of a resin material to make sure that it has certain, unique properties such as strength, stiffness and weight, or combinations of said properties, would enable material scientists to better develop the materials needed. Such monitoring would allow one skilled in the composite material art to successfully produce a material needed with less waste, and with the ability to identify any unfavorable properties of the composite material while it is in the production stage, as opposed to in the testing stage. It allows for variations in the production process to be made in the early stages of development.

The prior art teaches the use of fiber optics in detecting damage in composite structures. Hofer, in an article entitled "Fiber Optic Damage Detection in Composite Structures," *Composites*, Volume 18, No. 4 (September, 1987), describes a method for inspecting a composite material for remote damage. The method described utilizes surface mounted or embedded fiber optic cables. Similar to the present invention, the fiber optic cables can be drawn out to diameters comparable to that of the composite material reinforcement. Hence, the fiber optic cables can be embedded permanently in the composite without significantly influencing the overall integrity or properties of the composite material. Although the present invention may use the fiber optic cables described in the article, nowhere in the article is it taught that the fiber optic arrangement therein provides a means for determining resin location and cure during composite fabrication. Moreover, nowhere in the article is the grid-like system of the present invention set forth. The fiber optic system described in this article does not possess the novel features within the scope of the present invention.

A wide variety of devices already exist for monitoring the curing process of a wide range of resin materials. These existing devices utilize a variety of dielectric or microdielectric techniques to measure the electrical resistance or capacitance of the resin material being produced. The information obtained by these prior art techniques is then passed to a series of conventional signal conditioners, computer hardware and software. The conventional signal conditioners, computer hardware and software then interpret said information and displays it in a fashion which illustrates the curing process of the resin materials.

Prior art in composite monitoring utilizes the basic, conventional dielectric and microdielectric techniques. These techniques have been available, and have been used in the art for quite some time. Some patents illustrating the use of these well-known techniques are discussed below.

Senturia et al., U.S. Pat. No. 4,423,371, teaches a method for determining the moisture level in dielectric materials. The invention therein makes use of a well-known "comb" configuration in its monitoring apparatus. The "comb" configuration of Senturia et al. is illustrated in FIG. 2. The "comb" configuration enables the total dielectric sensing area to be increased. This configuration is used in the sensor device employed therein. Senturia et al., however, does not make use of the gap/grid concept employed by the present invention; and therefore, is unable to distinguish the location of varying moisture levels in said materials.

Day et al., U.S. Pat. No. 4,777,431, teaches an apparatus for monitoring dielectric changes in a wide variety of polymeric resin materials. The device within the scope of Day et al.'s invention is designed for sensing changes in the dielectric properties of materials undergoing state transitions such as resins undergoing curing. The invention includes the development of a semipermeable microdielectric sensor for use with graphite or ion graphing reinforcement and PMR-15 resin systems. PMR-15 resin systems are high temperature/high performance resins. The apparatus invented by Day et al, is adapted in such a manner that it is to be at least partially implanted into the material which is to be monitored. The sensor electrodes used in the patent are planar porous or mesh materials (see column 3, lines 52+). The sensor developed by Day et al., however, does not employ or teach the gap/grid encompassed by the invention herein. Moreover, the invention herein does not make use of conventional dielectric or microdielectric sensor materials.

The sensors taught in the above patents cannot be incorporated into the composite materials to be monitored in great number because of the size, cost, and limited means of attachment. Since these sensors cannot be incorporated into the materials in large number, the uniformity of properties of the composite material being produced cannot be accurately monitored. Moreover, the prior art sensors, even if they could be incorporated into the composite materials in great number, are prohibitively expensive; therefore, an alternate monitoring apparatus and method must be considered.

Berry, U.S. Pat. No. 3,383,863, teaches a method of detecting leaks in a pond, tank and pit. Berry makes use of a grid of electrical wires wherein the resistance between different wires of the grid are measured. It appears that the grid of electrical wires in said reference need not intersect with one another as one would expect in a conventional grid configuration. Note column 2, lines 65–70. Although Berry appears to teach the specific grid-like configuration employed by the present invention, nowhere does the reference suggest employing said grid-like sensor to monitor resin flow or resin cure. Moreover, Berry makes use of an ohmmeter. Use of the monitoring apparatus of the present invention, i.e., a scanner and/or computer device, are not even remotely suggested by the teachings in Berry.

The present invention offers an apparatus and method that is convenient, because of its use of conventional, electrically conductive, sensor threads; inexpensive, because of its maximizing the use of each sensor thread; and reliable. The sensing grid of the present invention can be embedded not only in the composite reinforcement, but it can be part of the bleeder, breather, and bagging materials, as well. The invention provides a means for monitoring resin migration during autoclave, hot press and other prepreg composite processes. The present invention provides a means for evaluating and monitoring thorough wet-out and cure, as well as a means for determining optimum mold and process configurations of the composite resin materials as they are being produced. Furthermore, the device can provide three dimensional flow field information, as well as local resin flow front velocities.

The present invention makes use of electrically conductive threads in a set grid-like configuration. The configuration used herein is considerably different from any resin cure or resin flow sensor previously used. The configuration of the sensors allows for more efficient monitoring of the resins using a minimal number of sensors threads. The cost of performing the monitoring function is, therefore, kept to a minimum. To date, an instrument for monitoring the cure of a wide range of resin systems using sensors that are incorporated as integral components of the composite resin structure has not successfully been proposed or accomplished. Moreover, a sensor system using a grid-like array of non-intersecting electrically conductive threads to serve as leads that can be connected to an interpreting apparatus (i.e. a computer) has also not been proposed.

Although grid-like electrically conductive devices have been employed in various art areas, they are herein applied for the first time in the monitoring of resin flow and resin cure. In addition, said grid-like electrically conductive devices to date have not been coupled with conventional scanner devices or computers. The present invention does not reside in the individual components of the electrically conductive device, the scanner or the computer. The invention resides in the combination of said conventional devices and in the use of said combination.

BRIEF SUMMARY OF INVENTION

This invention involves an apparatus and method for monitoring resin flow and resin cure as they occur in a resin composite fabrication process. More specifically stated, this invention relates to a method for incorporating a number of sensors into an uncured composite material, wherein said sensors are to remain an integral component of the material. The sensors herein can also be incorporated into the reinforcement, the bagging, the breather and the bleeder materials in a composite process. These sensors are incorporated in order to accurately and uniformly monitor, throughout the resin material, the flow front and cure of said material.

The purpose of the present invention is to provide a method for acquiring data regarding the resin location and its cure rate by a means which is both cost effective and efficient. This method employs the sensor apparatus of the present invention. The sensor threads to be used therein are conventional; and their use within the scope of the present invention renders the monitoring apparatus inexpensive. Moreover, these sensor threads are incorporated into the resin material structure in order to better access the properties of the resin and, therefore, allow one to obtain accurate data regarding the resin fabrication process.

The novel in-situ sensor system within the scope of the present invention has been given the acronym of S.M.A.R.T. (Sensors Mounted As Roving Threads) and is comprised to electrically conductive sensor threads arranged in a non-intersecting, grid-like configuration. The sensor threads do not intersect; however, they overlap one another. Where one would expect threads to intersect in a grid, there is a vacant space (herein referred to as "sensing gap"). For instance, threads which are perpendicular to one another may be in different horizontal planes.

The ends of each sensor thread herein is connected to a device that is able to continuously measure the electrical signal existing in the sensing gaps present between the perpendicular sensor threads. The types of electrical signals which may be continuously measured are resistance, capacitance, and dielectric measurements. As resin fills these sensing gaps, a measurable resistance, for example, is produced. The difference in resistance is processed, obtained and stored using a conventional multiplexer system and a computer storage system—such as FloWare ™, which is a process data acquisition system for resin transfer molding monitoring manufactured by Boeing Canada, Winnipeg, Canada. The FloWare ® system is used by Radius Engineering in mold flow visualization; however, this system, as employed by Radius, is not used throughout the composite thickness. It is merely employed on the surface of resin materials. From this stored resistance data, one can determine the resin flow location and the progress of the resin curve.

Use of the present invention allows for the accurate monitoring of the flow and cure of a resin material as it is being formed. In addition, its use permits one to better detect uniformity of the properties within the resin composite material produced.

Accordingly, it is an object of the present invention to produce an efficient and accurate apparatus and method for monitoring the flow and cure of a resin composite material.

A further object of the invention is to provide an economical means to utilize conventional sensor threads.

A further object of the present invention is to produce an efficient sensor means which may be incorporated as an integral component of a composite structure.

A further object of the invention herein is to produce an efficient sensor means which may be used in a variety of composite processes (i.e. bleading, bagging, molding, curing, etc.) and composite processing materials.

Still, a further object of the present invention is to optimize the use of conventional sensor threads by arranging them in a non-intersecting, grid-like manner.

A further object of the invention is to produce sensors which are structurally compatible with the resin composite material so that the sensors may even assist in reinforcing the material structure.

A further object of the present invention is to provide a means for intelligent control of composite fabrication processes wherein the invention herein described provides critical manufacturing information.

Other objectives and features of the present invention will be apparent from the following detailed description of the invention and claims herein.

DETAILED DESCRIPTION OF INVENTION

The invention, which is a sensor system, allows one to monitor resin flow and the curing of resins. The invention is primarily utilized to monitor said parameters during the fabrication of composite materials.

The general purpose of the invention is to allow the acquisition of a substantial amount of data regarding the location of a resin material and the cure rate of said material. This purpose can be attained through cost effective means using efficient sensors that are incorporated into the resin composite structure as integral components thereof. The sensor system may be used in a variety of composite processes for various purposes, such as, resin location, cure monitoring, and feedback for autonomous or partially autonomous processing. The sensor system can additionally be used to optimize the composite process by reducing waste and time since the sensors can specifically pin-point the location of any material problem.

The invention, which is set forth in FIGS. 1-9, comprises an array of non-intersecting, electrically conductive threads which are embedded into or placed between the constituent composite fabric. The individual electrically conductive threads serve as leads which are connected to a multiplexer/rapid switching system. These threads may be connected to said system using conventional means, such as, clamps, contacts or ports.

Composite resin, in its liquid form, typically has a low electrical resistance relative to that of its fully cured state. For example, in its liquid form, a resin such as 4102 Cycom® (manufactured by American Cyanamid of Saugus, Calif.), may have an electrical resistance ranging from approximately $10^6$ to $10^{11}$ ohms; while in its cured state, the same resin may have an electrical resistance which ranges from about $10^{12}$ to about $10^{15}$ ohms. As a resin saturates the composite fabric mentioned above, the gap between the non-intersecting, perpendicular conductive threads is filled. As this gap is filled with resin, a measurable electrical resistance is produced. A connection is made by the resin between the conductive threads and a device which is able to measure the electrical resistance produced. The electrical resistance is measured using a conventional analog/digital multimeter which measures the resistance via a conventional multiplexer/rapid switching system. The conventional multiplexer performs the necessary function of rapid and continuous switching of line signals, which in turn allows for the thorough and complete monitoring of the entire sensor field and helps facilitate the storage of the data obtained onto a computer system. This system is a conventional component that allows the entire number of sensing gaps to be monitored. It is simply a switching apparatus designed to interface with and be controlled by a computer.

Once the multiplexer/rapid switching system selects a certain sensing gap to monitor, the objective becomes that of obtaining and storing the signal received from that sensing gap. This signal, which may be analog or digital in nature, is then conditioned by a multimeter scanner. The multimeter scanner converts an electrical signal received into an interpretable and meaningful number corresponding to the variable of interest to be monitored. For our purposes, for example, the variable of interest may be the measurement of resistance.

Use of a multiplexer/rapid switching device enables one to obtain a vast number of data relatively few data logging channels. This signal is then converted by the scanner to digital format so that the computer can comprehend it. Once the signal is converted into "readable" form, computer software is used to manipulate the data to form a plot or display of the data received onto a screen. This data can be stored by the computer in the conventional fashion. The invention herein resides in the grid-like, sensor system combined with a data acquisition and processing system and its use. The acquisition and processing components (i.e., multiplexer, scanner, personal computer, etc.) are conventional components and are merely described so as to enable one having skill in the art to determine the types of conventional data acquisition systems which may be used herein. One of the novel features of the present invention is the manner in which the multiple sensor system is constructed so as to be structurally compatible with the resin composite material. The sensor system of this invention is embedded into the resin material and remains an integral component of the resin. Among the materials from which the grid-like, sensor system may be constructed are graphite, metallic fibers such as lead-coated glass, aluminum, copper, etc., and electrically conductive polymers such as conductive-ink enriched polyester, or other organic or inorganic materials having like properties. Basically, any electrically conductive material that can be manufactured into a thin fiber form can be used herein. The electrically conductive material selected may be used alone as a sensor thread or may be coated onto a reinforcement material which is then arranged in the configuration within the scope of the present invention.

The particular material to use as a sensor thread should be chosen in order to accommodate the specific resin composite process to be performed and the particular variable to be monitored by the system. Sensor materials within the scope of the present invention may include materials that are conventionally used as reinforcement or matrix materials in the resin arts. If, a sensor material is chosen which also has reinforcement properties, then the mechanical properties of the resin composite will be enhanced. The selection of the particular sensor material is important because it will, as previously stated, remain an integral part of the resin composite after the processing (i.e., curing) has been completed.

The sensor threads may be used alone or coated onto a reinforcement thread to produce the sensor system or they may be woven into or placed between successive layers of threads within the sensor system herein are placed such that they do not physically intersect and are perpendicular with sensor threads both above and below them. The arrangement of the sensor threads in the system create a grid-like configuration as set forth in FIG. 3. The invention herein should not be limited to the perpendicular, grid-like configuration described above and depicted in the drawings. Other geometries, such as irregular grid-like patterns, are well within the scope of the present invention.

These electrically conductive threads, for example purposes only, may have a tow diameter ranging from about 0.2 cm to about 0.8 cm. The length of said threads may range from about 0.5 m to about 10 m. The distance between two, side-by-side, parallel electrically conductive threads should be approximately 20 times that of the diameter of the threads employed in the sensor. This distance usually is about 2.5 inches. The distance of the sensor gap should be less than about 5 times the diameter of the threads employed in the sensor. This sensor gap distance usually ranges from about ⅛ inches to about 3/16 inches. Perpendicular, electrically conductive sensor threads should never touch, not even under compressive loading conditions. These measurements are set forth for example purposes only; and should not be interpreted as being the limits of the scope of the protection sought by the present invention.

The ends of each sensor thread are then connected through a multiplexer/rapid switching device to a conventional scanner. A scanner has the capability of continuously measuring the electrical resistance, for example, present in the gaps between the perpendicular sensor threads. The sensor system of the invention operates in the following manner: Resin is allowed to flow into a mold, for example, already having the grid-like sensor device placed therein. The resin flows filling the sensor gaps existing within the sensor system. The gaps between the two perpendicular, non-intersecting conductive threads represent the minimum path of resistance. Hence, as the resin fills the gaps, the minimum path of resistance occurs. This resistance measurements or reading is what is sensed by the scanner. The uncured resin fills the individual gaps within the system, which produces a measurable resistance. This resistance indicates that resin has reached the particular location wherein the gap is present. Therefore, the flow front of a resin material can be followed. As the composite production process proceeds, the resistance measurements at said gaps change.

The present invention provides a unique, low cost, and efficient means for continuously monitoring the resin front and the resin cure progress. The computerized data acquisition systems generally described herein are conventional to the art. One can employ, for example, a FloWare ™ RTM (Resin Transfer Molding) Process Data Acquisition System (manufactured by Boeing Canada, Winnipeg, Manitoba) as the computerized data acquisition system herein. These types of computerized data acquisition systems are capable of scanning, monitoring and displaying resistance changes from approximately 50 sensor gaps in approximately one to ten seconds.

Figure 2:
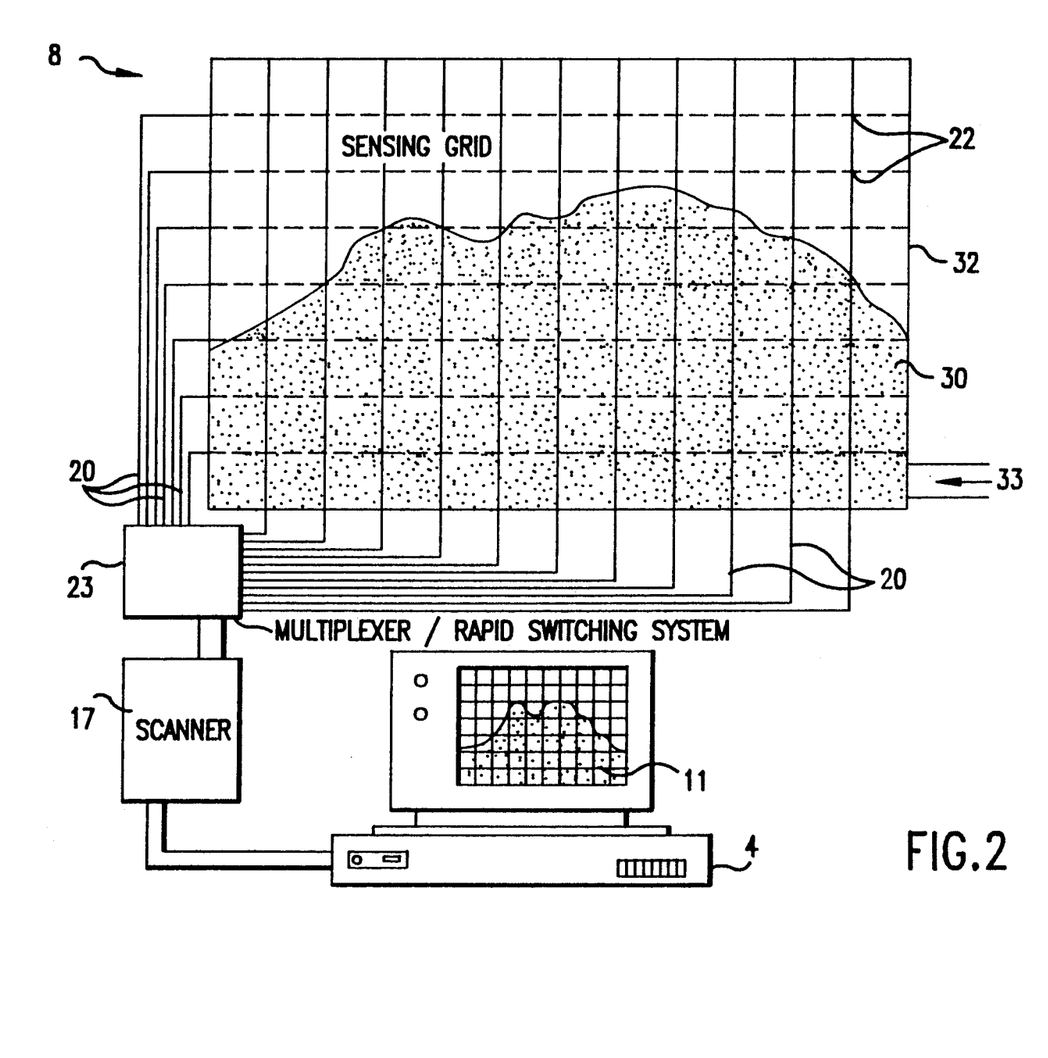
FIG. 2 illustrates a schematic diagram of the apparatus herein as it is used along with conventional reading and monitoring equipment (i.e. computer).

In sum, the change of resistance and capacitance at each of the sensor gaps may be registered by a conventional multiplexer, scanner and computer storage system (see FIG 2). The information obtained by the use of this process and apparatus provides a material scientist with at least two critical pieces of information—resin location and cure progress. Application of the present invention permits one to easily and efficiently obtain these pieces of information over a large number of reference points in the composite resin material.

Furthermore, having obtained the above described information, along with the resin front location, it is also possible to calculate the resin flow front velocities. This is an additional distinguishing characteristic of the present invention over the prior art.

Three dimensional resin flow location can be determined by employing the present invention. As the resin is filled into the grid-like sensor system, before it reaches the sensing "gap," the resistance measurement is essentially, for all practical purposes, indefinite. This indefinite reading indicates that the resin flow front has not yet reached the sensor "gap." Once the resin fills the "gap" between perpendicular, spaced threads, a resistance measurement can be made and changes from this initial indefinite reading to the filled "gap" reading allows the skilled materials scientist to determine the flow location of the composite resin.

In addition, from the measurement of the resistance between the "gap" as the resin process progresses, one skilled in the materials art can determine the cure progress of said resin. As resin cures, it typically exhibits a substantial increase in electrical resistance measurements. From the resistance measurement readings, it is possible to determine the cure rate and progress at each of the multiple sensor "gap" locations. This may be performed by following the resistance change throughout the course of a composite process.

The multiple sensing apparatus and technique of the present invention may be employed with any composite resin system that exhibits electrical conductivity in its uncured, liquid state and through its transition to a viscoelastic, cured solid. The present invention is able to monitor resistance, capacitance and dielectric signals. Typical electrical resistance measurements, for example, which may be observed and monitored range on the order of $10^4$ ohms to $10^{12}$ ohms. In order to effectively monitor the change in resistance, the electrical resistance of the sensor reinforcement must be at least an order of magnitude greater than that of the resin in its cured state. The path of least resistance in the process is monitored and defined by each sensing "gap."

The advantages of the present invention can be understood by briefly examining the existing methods and equipment used in the monitoring of resin cure. The existing methods have been, as previously stated, prohibitively expensive. The prior art methods do not reveal a method for conveniently locating resin advancement in wet composite processes such as resin transfer molding. Discrete sensors, of the prior art, such as conventional dielectric and microdielectric sensors are too bulky to be incorporated in a resin monitoring apparatus in great numbers. Moreover, dielectric and microdielectric sensors require electrical leads that are, at least, directly proportional to the number of sensors used, as in the case of RTM (resin transfer molding). The apparatus of the present invention uses a more advantageous means of accomplishing the desired monitoring. This means is the grid-like, matrix arrangement described above.

By using the grid-like arrangement as described, the sensing field within the composite resin is more efficient in that the number of monitoring areas, the sensing "gaps," are increased. The efficiency of the monitoring apparatus is increased as the number of sensor "gaps" is increased. For example, in the present invention, from about 40 to about 50 sensor locations may be present in a resin having the dimensions of one meter by 0.7 meter by 6 cm. To accomplish the same monitoring effect, the prior art monitoring apparatus would require a greater number of sensor threads than that required in the present invention. The present invention maximizes the monitoring ability of sensor threads by their specific arrangement. The following expressions describes the relationship of sensors to individual leads. You will note that in the prior art methods, the number of sensing leads has at least twice the number of sensor points (or "gaps" as referred to in the present invention). In the present invention, however, a greater number of sensor points, "gaps," exists.

Total Number of Sensing Leads = R + C

Total Number of Sensing Gaps = R × C

Figure 4:
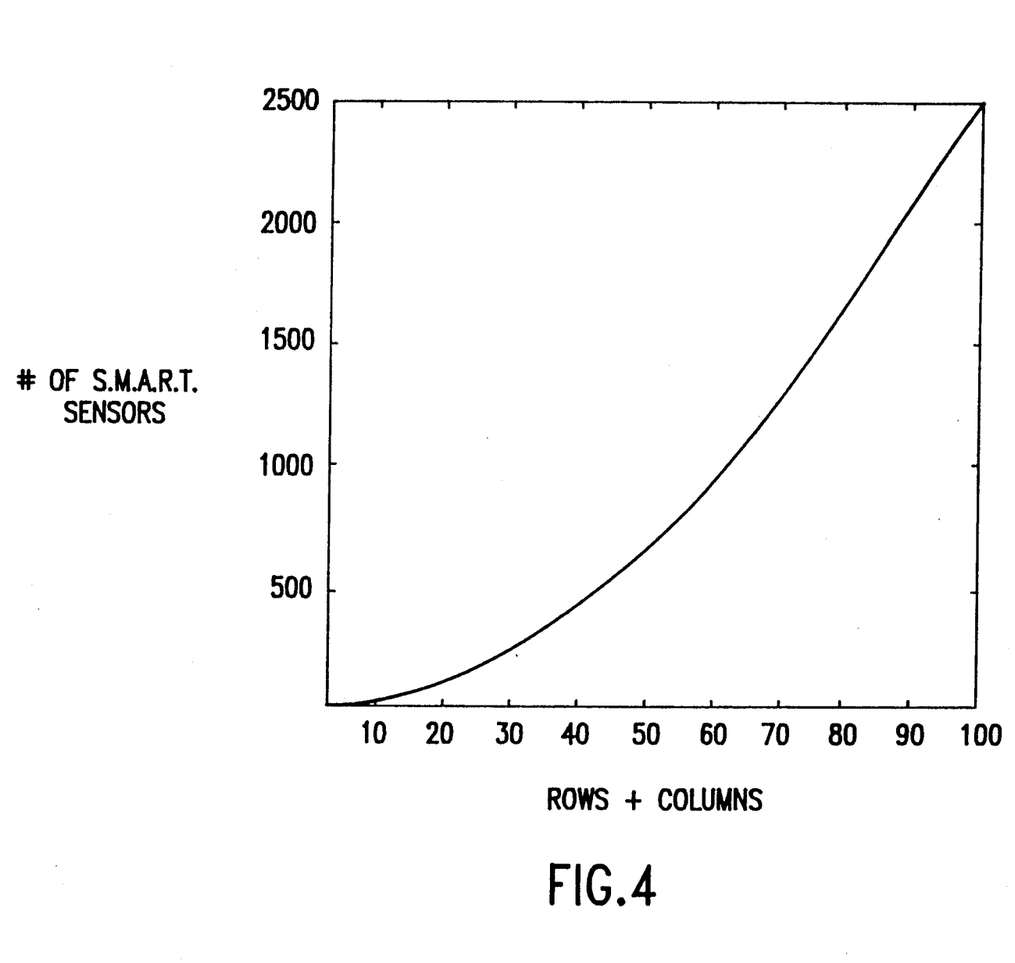
FIG. 4 is a graphic representation of the relationship between (rows+columns) to (rows×columns) to illustrate sensor points.

In these expressions, R represents the total number of rows and C represents the total number of columns. FIG. 4 illustrates how a grid-like array of threads (row and columns) creates a large number of sensing "gaps." For example purposes, note that 50 rows of threads and 50 columns of threads produce 2,500 sensing "gaps." The configuration of and the invention itself is has been named the S.M.A.R.T. (Sensors Mounted as Roving Threads) monitoring system.

A further example to indicate the advantages of the present invention optimizing the number of sensor "gaps" is as follows: In the conventional sensor methods, if it was necessary to insert nine (9) discrete dielectric sensors into a composite resin material, one would require the use of at least eighteen (18) leads. Conventional dielectric sensors have at least two leads per sensor. In the exercise of the present invention, since a grid is created by overlapping conductive strands, only three rows and columns are required to create nine novel sensing "gaps." Therefore, one can see that in order to accomplish the same monitoring task of a resin, the conventional dielectric scheme requires 18 leads, whereas the leads required in the present invention would only be six. The ratio of sensors to leads for the conventional dielectric sensor is 9:18; whereas, the ratio of sensors to leads for the apparatus of the present invention in this example would be 9:6. By using a matrix grid-like arrangement to create the sensing gaps, the sensing field is made more efficient with increasing the number of sensing gaps. This illustrates the dramatic advantage of the present sensing gap/grid system over the use of the conventional sensors already on the market.

Several patentable features and concepts are incorporated into this invention. First, the sensing material can be composed of a variety of electrically conductive materials such as graphite, metals, alloys, powder coatings, metal oxides, such as lead and copper, and conductive polymers. These sensing materials, in fiber form, can either be used alone or coated onto conventional reinforcement fibers, such as glass. The sensing material can be woven or placed in the reinforcement, thus creating sensors from materials that are already structurally compatible with the composite resin and resin reinforcement materials. Moreover, the concept used to create sensing gaps is unique. The grid concept allows for the efficient, cost effective creation of a large number of sensor "gaps" with few leads. The sensing grid is, therefore, deemed to be more efficient than the prior art monitoring devices. The more sensors employed in the sensing grid, the more efficient the monitoring device/system employed.

The invention is well suited for use in monitoring the manufacture of composite resin materials wherein a high degree of accuracy in monitoring the complete curing process is needed. This assures uniformity throughout the resin product. Use of the present invention in composite resin fabrication will reduce the amount of waste associated with the production of poor wet out and/or cure. Moreover, the information one is able to obtain from the use of the present invention during the process of making composite resin materials is invaluable. The information could be used by the materials scientists to optimize the process employed.

The inventor has invented an inexpensive, flexible method for monitoring both composite resin location and cure.

DETAILED DESCRIPTION OF THE DRAWINGS

Figure 1:
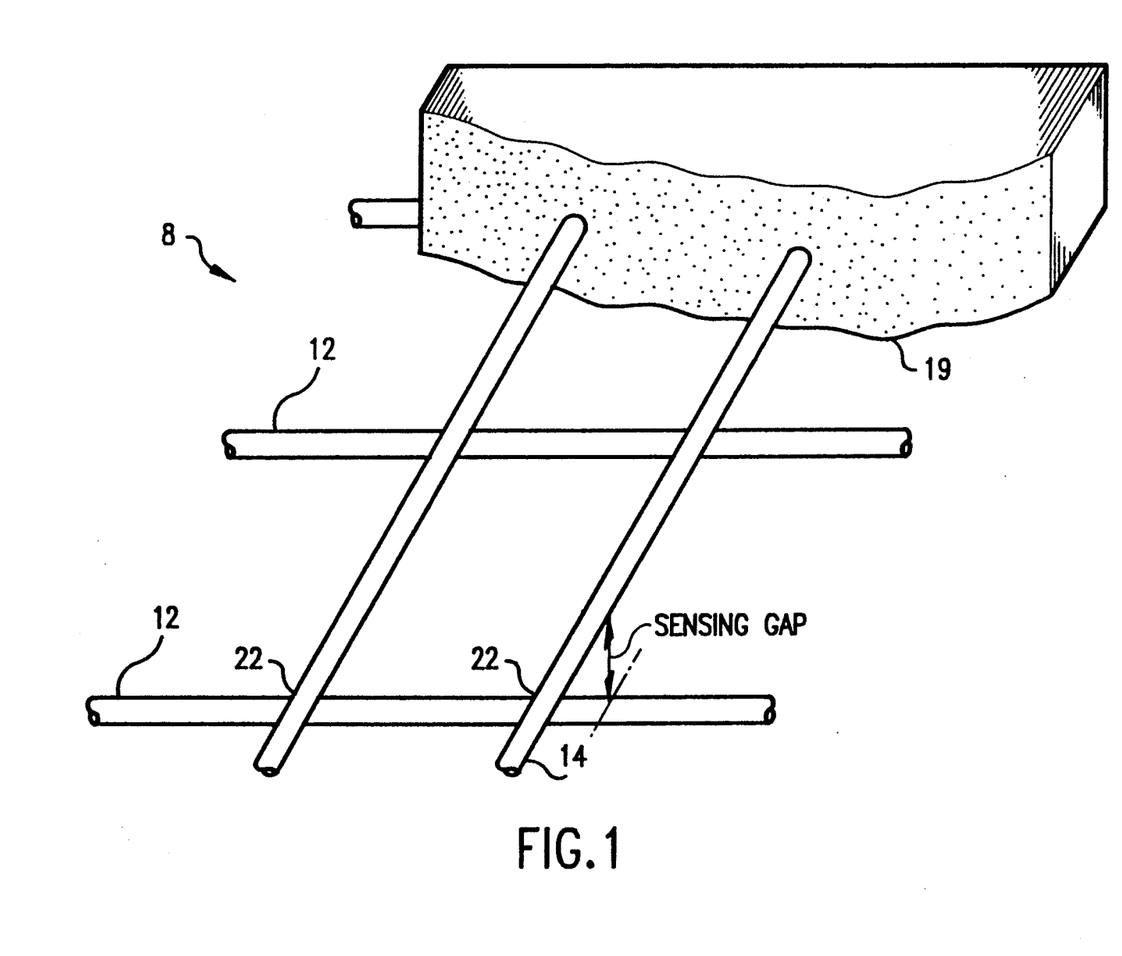
FIG. 1 illustrates a schematic diagram of the apparatus within the scope of the invention in use.

FIG. 1 illustrates a schematic diagram of the grid-like monitoring apparatus 8 within the scope of the present invention. It shows electrically conductive threads 12 and 14 in a non-intersecting, grid-like configuration. Note that the spaces (voids) 22 between the perpendicular electrically conductive threads 12 and 14 represent the sensing "gaps." The grid-like monitoring apparatus of the present invention 8 is used, as already stated herein, to monitor the resin front 19 and the cure rate.

FIG. 2 illustrates a schematic diagram of the grid-like monitoring apparatus 8, containing sensing gaps 22, as it is used to monitor the information sought. Resin 30 is pumped from resin supply port 33 into a mold 32 containing monitoring apparatus 8. The resin 30 advances through the sensing grid monitoring apparatus 8. Leads 20, which are also the threads which make up sensing grid 8, are connected to the perimeter of mold 32 by conventional means. The leads 20 are connected in such a manner so as to facilitate the non-intersecting, grid-like configuration of monitoring apparatus 8. The ends of the threads which make up sensing grid 8 serve as leads 20 which all converge and join at a conventional multiplexer/rapid switching system represented as 23. The multiplexer/rapid switching system 23 in turn transmits a resistance signal, for example, obtained from the sensing grid's sensor gaps 22 to a scanner 17. The scanner 17 translates the signals for the computer 4. The computer 4 is then able to interpret the resistance signal and display it onto its graphics window 11.

Figure 3:
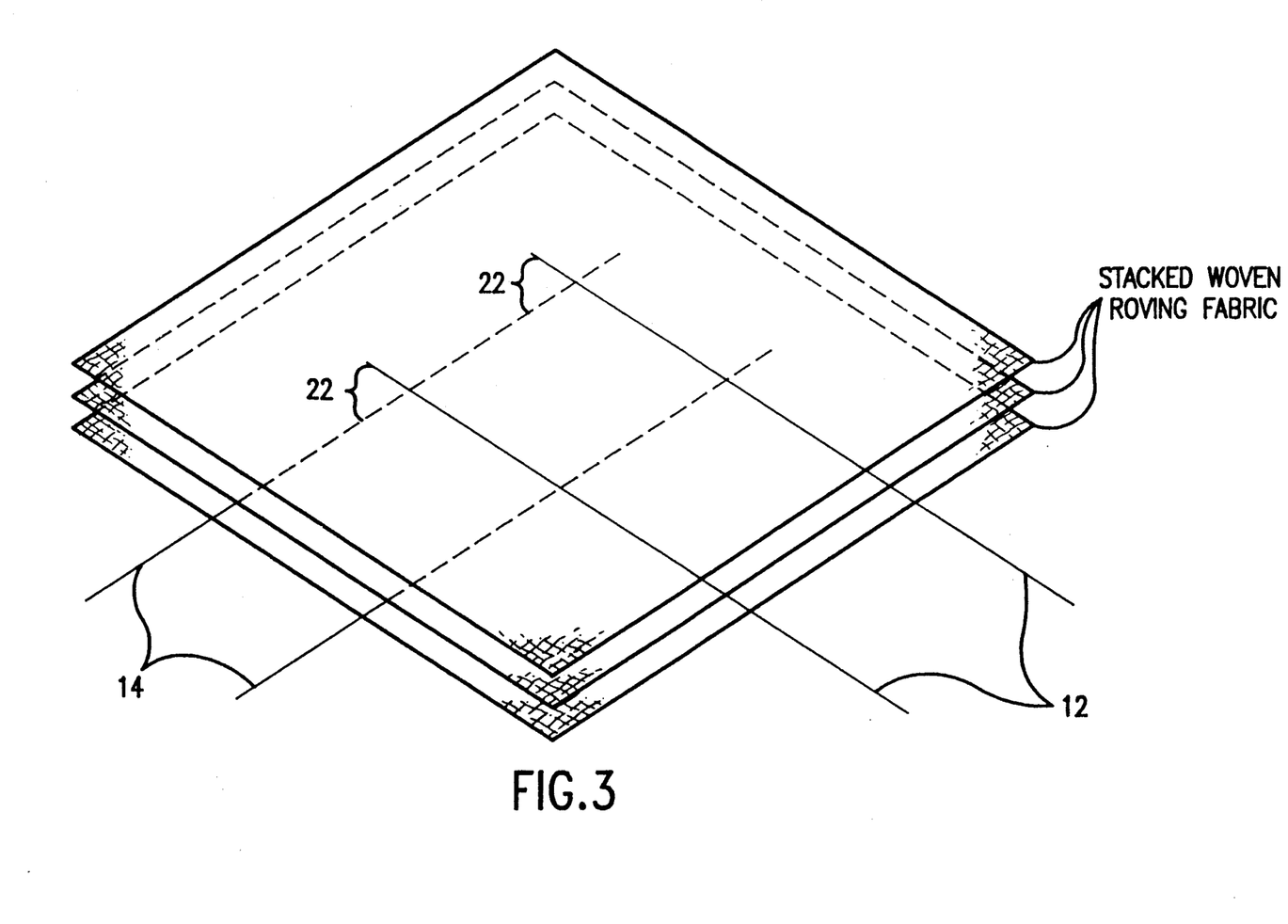
FIG. 3 represents another schematic diagram illustrating a three-dimensional view of the application of the present invention.

FIG. 3 illustrates a more detailed or possibly another representation of the grid-like monitoring system set forth in FIG. 1. It illustrates electrically conductive threads 14 and 12 in a perpendicular, non-intersecting configuration. Note that electrically conductive threads 12 are on a different plane than electrically conductive threads 14. Hence, they do not intersect or touch. The gaps between said threads 12 and 14 is referred to herein as a sensing gaps 22. It is at sensing gaps 22 where the resistance is measured when employing the present invention.

FIG. 4 has previously been described herein. It is a graphic representation of the relationship between the number of sensing gaps in the S.M.A.R.T. system to the number of sensor leads present. Note how a limited number of sensor leads, shown on the x-axis, are able to establish large numbers of sensing gaps. FIG. 4 generally illustrates how a grid-like array of threads creates a larger number of S.M.A.R.T. sensing gaps. For example, note that if one were to have 50 rows of thread and 50 columns of threads (totalling 100 rows and columns), 2,500 sensing gaps would be produced using the present invention.

The number of sensor "gaps" within the scope of the present invention far exceeds the number of sensing means of the 2-lead sensors. If 20 data points are obtained using a 2-lead system, for the same number of sensor threads merely arranged in the invention's S.M.A.R.T. (Sensor Mounted As Roving Threads) grid-like fashion, 400 data points are obtained.

Figure 5:
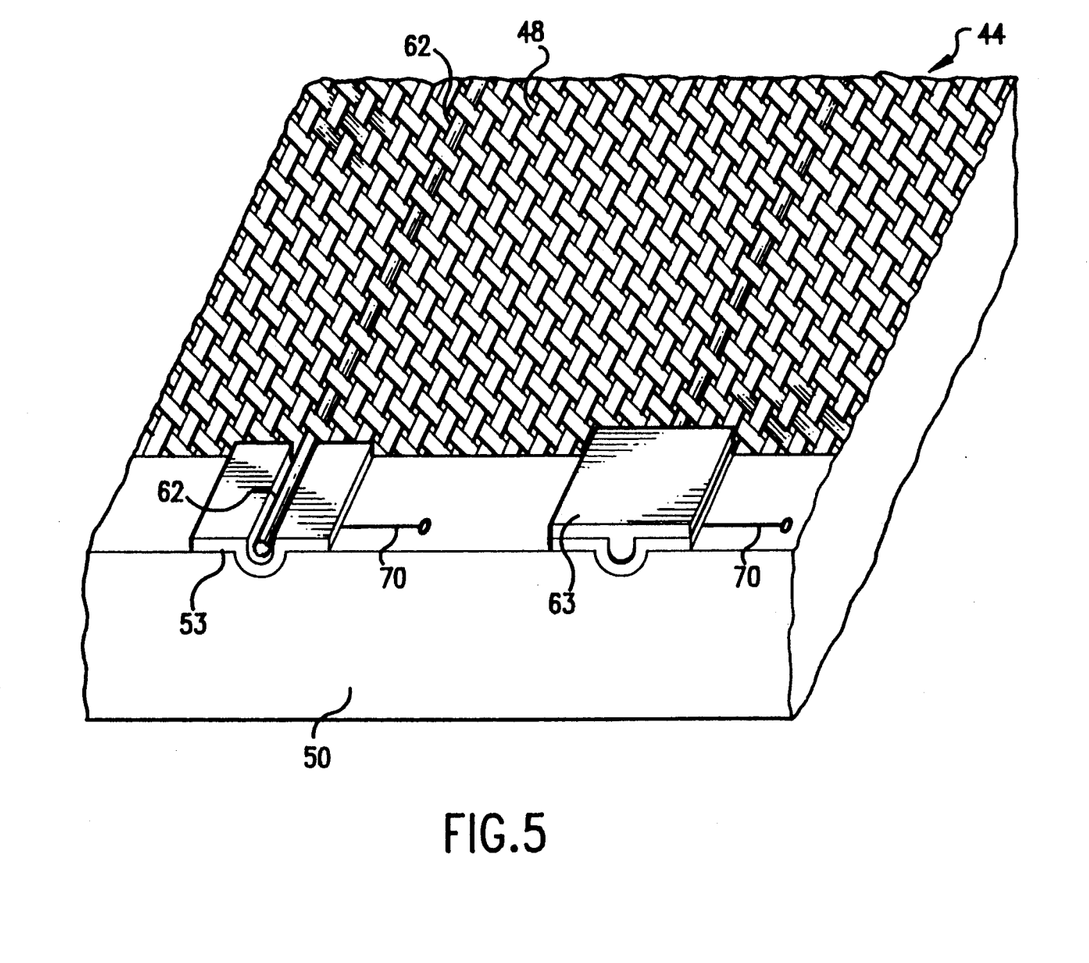
FIG. 5 illustrates how a sensor grid within the scope of the invention is connected for use.

FIG. 5 illustrates how the S.M.A.R.T. weave system 44 can be easily and readily employed. The grid-like material set forth in the S.M.A.R.T. weave system 44 comprises constituent reinforcement fibers 48 and electrically conductive fibers 62. The constituent reinforcement fibers 48 may be composed of materials such as woven, roving glass fiber; the electrically conductive fibers 62 may be composed of materials such as graphite fiber. Note that the electrically conductive grid lines 62 are embedded or enmeshed into the constituent reinforcement materials 48. Said electrically conductive grid lines 62 are arranged in a grid-like configuration; however, where the location in which an ordinary grid would intersect, the fibers 62 do not even touch. The S.M.A.R.T. weave system 44 is placed into a mold 50, which is to house a resin material (not shown) to be cured. Note that the mold 50 is equipped with a female electrical connecting pad 53 and a male electrical connecting pad 63. Both of these connecting pads 53 and 63 may be composed of materials such as a copper film backed with a compliant foam adhesive. From said connecting pads 53 and 63, signal lines 70 are used to relay the resistance, capacitance or dielectricity experienced at each of the non-intersecting sensing gaps of said S.M.A.R.T. weave system 44. These signal lines 70 are connected to a programmable intelligent computer circuit (not shown).

Figure 6A:
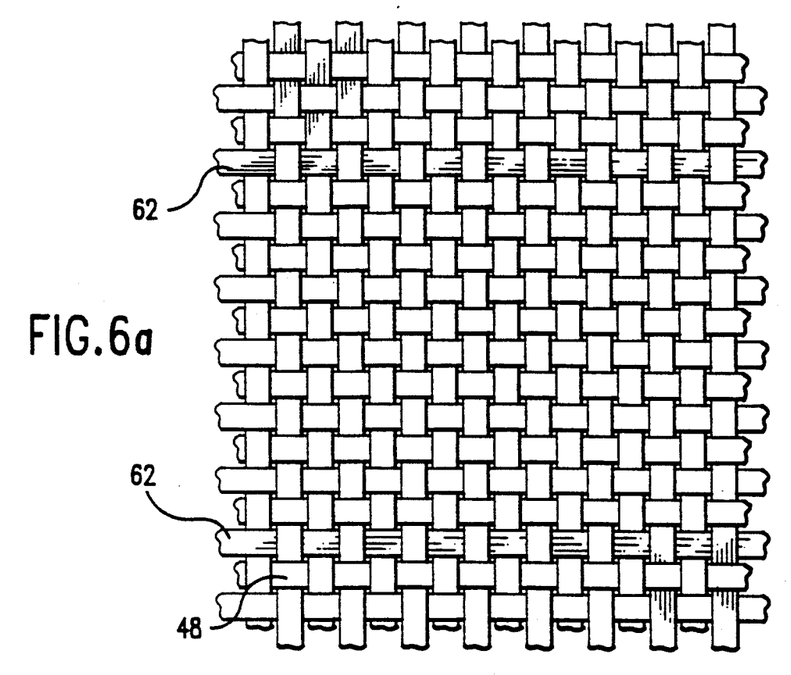
FIG. 6 is an illustration of the ease of obtaining electrically conductive leads from the grid-like sensor system of the present invention.
Figure 6B:
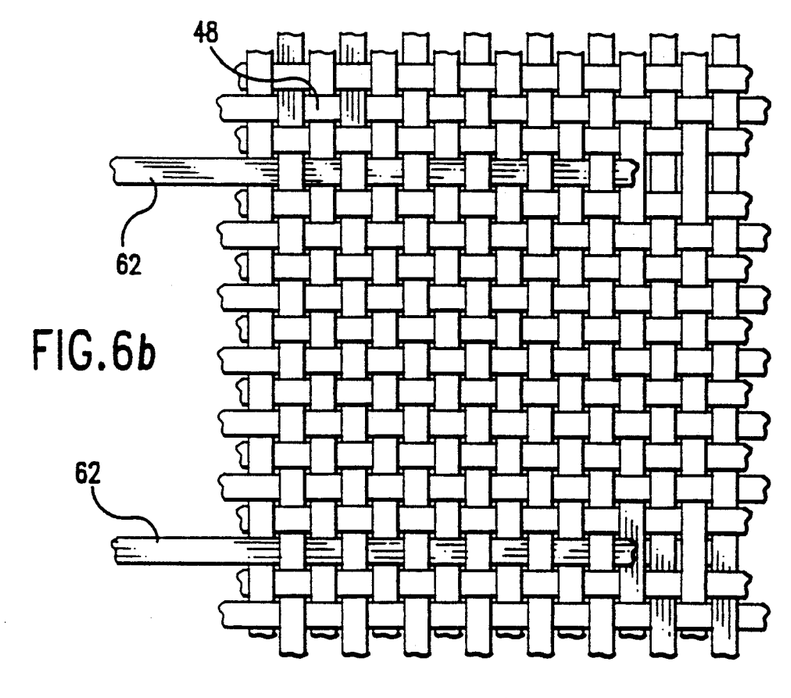

FIG. 6 illustrates the ease of obtaining electrically conductive leads 62 from the grid-like sensor system of the present invention. FIG. 6a illustrates electrically conductive lead 62 woven into fabric bulk reinforcement 48. FIG. 6b illustrates electrically conductive leads 62 after they have been displaced from the bulk reinforcement material 48. The electrically conductive leads 62 are to be connected to a scanner (not shown).

One can note that the electrically conductive leads 62 can easily be displaced from the constituent fabric bulk reinforcement 48 so as to allow for the electrically conductive lead 62 to be exposed for easy hook-up to the electrical connecting pads 53 and 63, as set forth in FIG. 5.

Figure 7:
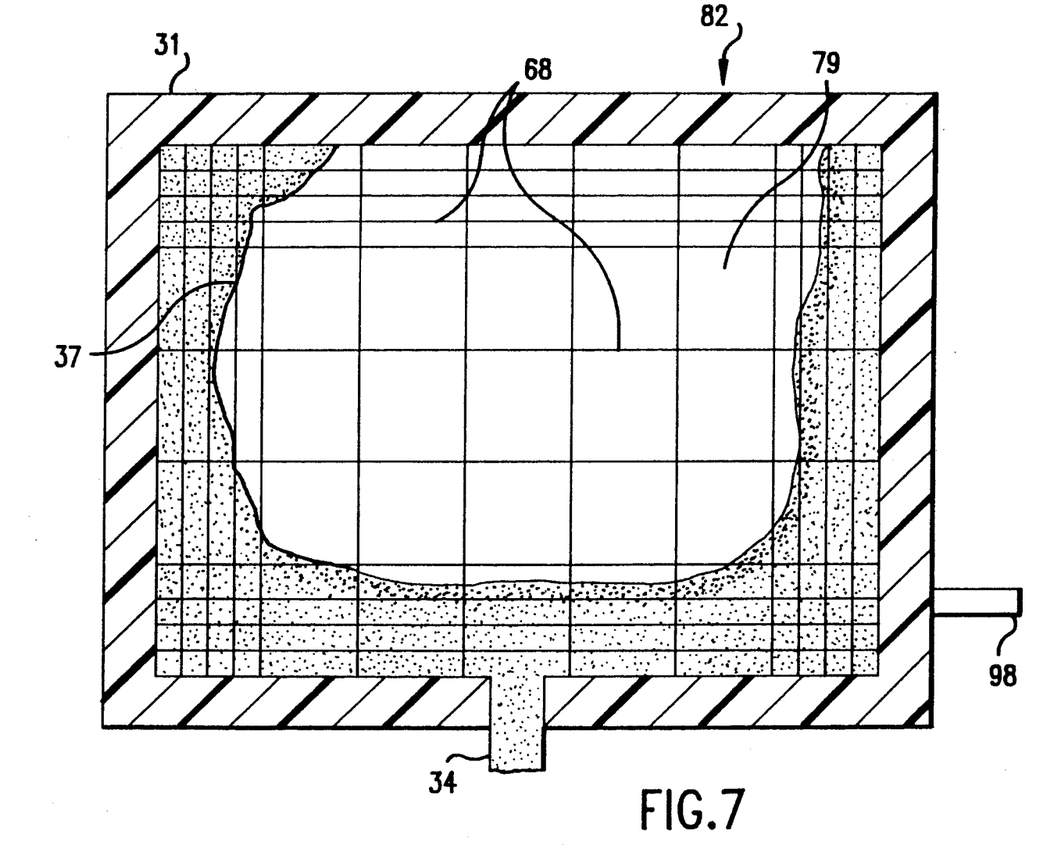
FIG. 7 illustrates the resin flow and cure sensing grid of the invention in actual use. Note that the grid may take on an irregular, non-uniform configuration.

FIG. 7 illustrates the resin flow and cure sensing grid 82 as used by the present invention. Note that fabric reinforcement material 79 has embedded therein electrically conductive sensing grid leads (or threads) 68. Note that said electrically conductive sensing grid leads 68 need not be uniformly placed throughout the cure sensing grid 82. The electrically conductive sensing leads 68 are placed in a non-uniform fashion throughout the cure sensing grid 82. The cure sensing grid 82 can be constructed in such a way so as to maximize its potential within a given composite process scenario. In FIG. 7, the electrically conductive sensing grid leads 68 are arranged in such a fashion so as to produce a cure sensing grid 82 which is extra fine around the perimeter of the resin transfer mold 31. The cure sensing grid 82 design is illustrated in this fashion since the flow of resin 37 is usually rapid in the perimeter region of the resin transfer mold 31. Therefore, a more accurate flow and cure sensing reading can be obtained around said perimeter region.

FIG. 7 additionally teaches an example of one of the many locations in which a resin injection port 34 may be placed onto a cure sensing grid 82 of the type herein. Moreover, set forth in FIG. 7 are grid lines 98 which are to be connected to a scanner (not shown).

Figure 8:
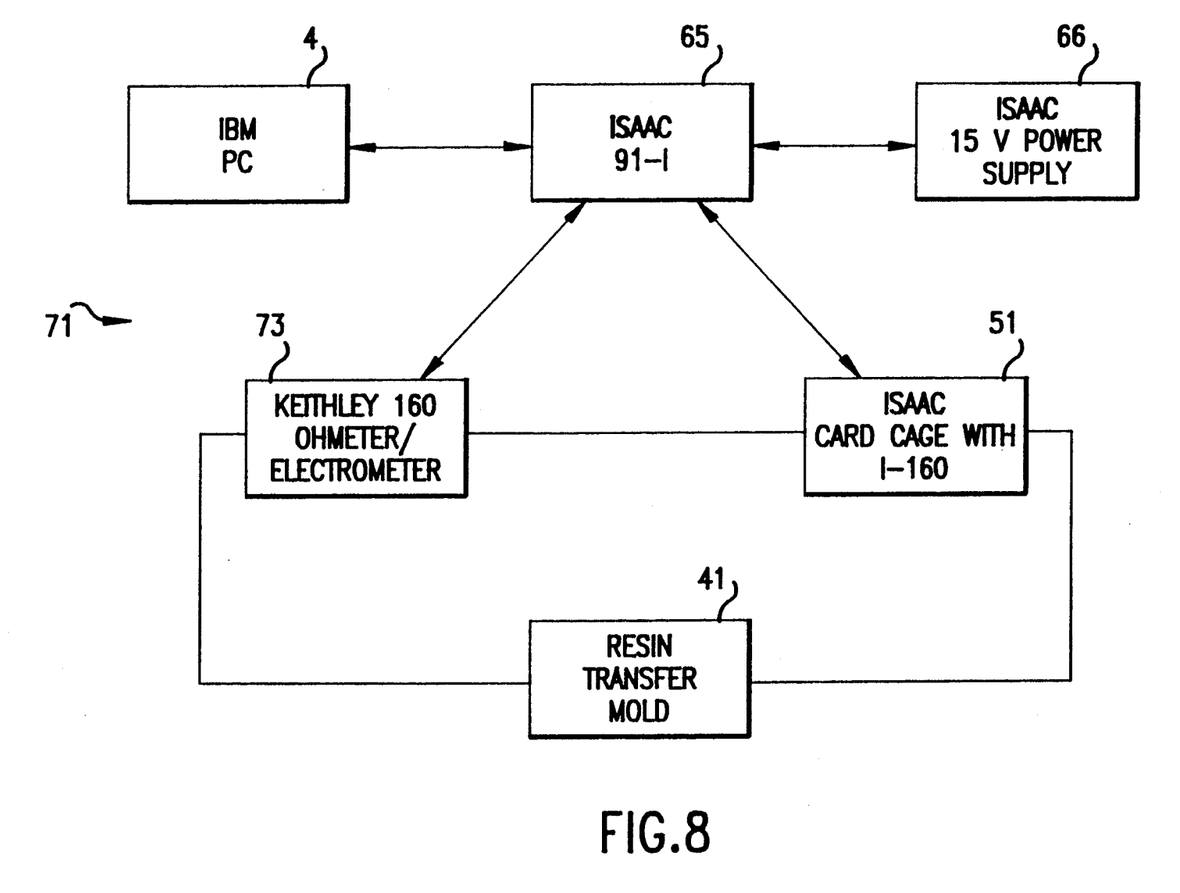
FIG. 8 illustrates a specific embodiment of the present invention.

FIG. 8 is an illustration of one embodiment within the scope of the present invention. Said Figure illustrates a resin flow and cure sensing apparatus comprising a resin flow and cure sensing device 71 which consists of a resin transfer mold 41 wherein the electrically conductive leads are arranged in a non-intersecting, grid-like fashion (not shown). The apparatus 71 further comprises, in the configuration set forth in FIG. 8, a Keithley 160 Ohmeter/Electrometer 73 which is manufactured by Keithley Instruments, Cleveland, Ohio, and serves the function of obtaining the raw electrical signals from the sensor grid; an Isaac Card Cage with I-160 51, manufactured by Cyborg Corporation, Newton, Mass., and serves the function of multiplexing through the sensing threads, which provides thorough interrogation of the sensor grid; Isaac 91-I 65, manufactured by Cyborg Corporation of Newton, Mass., and serves the function of data acquisition; an Isaac 15 Volt Power Supply 66, manufactured by Cyborn Corporation, and serving the function of powering the scanning system; and finally an IBM personal computer, manufactured by International Business Machines of Boca Raton, Fla., which displays and records data. This illustration is merely one example as to how the invention herein may be used and operated.

Figure 9:
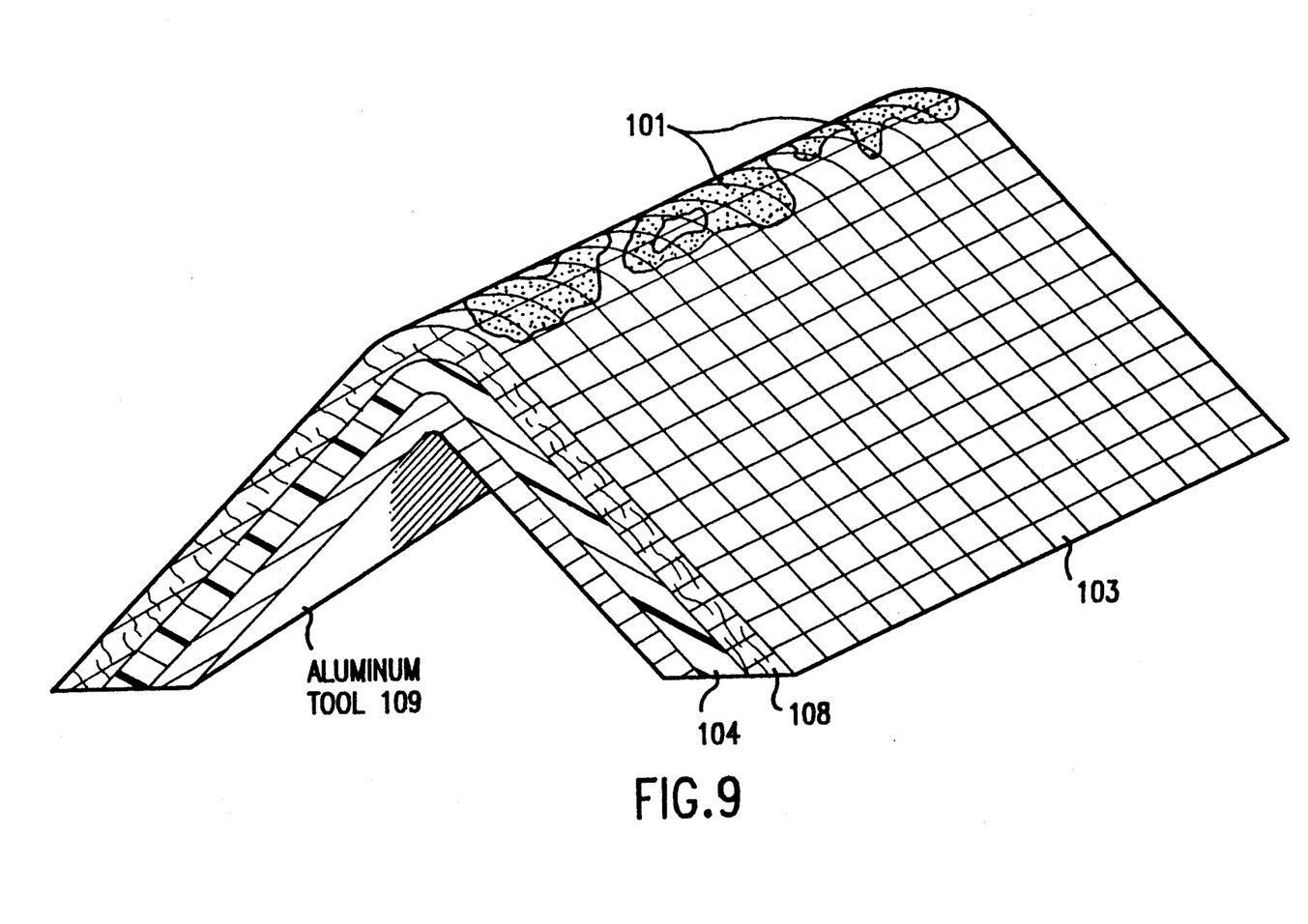
FIG. 9 illustrates the use of the present invention in a bleeder-type composite process.

FIG. 9 illustrates the deployment of the present invention in a bleeder-type composite processing configuration, as distinguished from the resin transfer molding discussed above. The illustration is provided to point out that the present invention is not limited to resin transfer molding processes. In the process which the invention is depicted in FIG. 9, the flow of the resin is based on the principles of permeation, as opposed to pressure or injection. Sensing grid 103 is used to monitor the progress of bled-through epoxy resin 101. Note the graphite/epoxy layer 104 which is bled through bleeder layer 108, and which then comes into contact with sensing grid 103. The bleeder layer 108 may be composed of conventional absorbant bleeder materials such as absorbant glass and burlap. The invention, when employed in the bleeding process, is capable of indicating where excessive and mild bleeding of resin occurs in the laminate.

The present invention may be further described by way of example; however, the example set forth below in no way is to be construed as limiting the scope of the invention herein.

EXAMPLE 1

The invention herein was successfully used to monitor the flow of a non-Newtonian polyester resin by the tradename Stypol® 40-4200 (manufactured by Freeman Chemical Corporation). The monitoring of the flow of said polyester resin was performed through porous woven, roving S2-glass (manufactured by Owens Corning Corporation of Ohio) having a satin weave. A rectangular resin transfer mold having the dimensions of 36 inches by 24 inches by 2 inches was used to produce a uniform resin block. The transfer mold utilized was composed of an epoxy and had excellent electrical resistance.

Before the actual pouring of the resin into the mold, the non-intersecting, sensor grid was implanted into the S2-glass fabric which is then placed into the mold in a laminated fashion (layer by layer). The sensor grid was implanted into the S2-glass fabric so as to produce a square grid arrangement, wherein each square formed has the dimensions of 4 inches by 4 inches. The material which was used to make up the sensor grid was graphite fiber (manufactured by Gear Lakes Corporation Fortafil of Elizabethton, Tenn.) in a multi-strand tow, wherein the tow had a diameter of approximately 0.27 inches. The ends of the electrically conductive graphite grid fibers were threaded around the mold O-ring so as to maintain a good seal as well as allow for the fibers to be connected to a scanner device.

The location of the sensing grid of the mold was placed in the center of the mold—approximately one inch above the bottom surface and consequently about one inch below the top surface of said mold. Moreover, as set forth in FIG. 8, an Isaac 91-I along with an Isaac Card Cage with I-160, together with a link MUX (term of art for a multiplexer, such as the Isaac 91-I) and gang relay were configured to provide the IBM PC with the raw electrical signals from the sensing grid 41. FIG. 8 illustrates a schematic diagram detailing the means by which the sensing grid is scanned and data is obtained and displayed—i.e. on a PC.

A Loggernaut® data acquisition system, manufactured by Cyborg Corporation, Newton, Mass., and specifically developed BASIC-based software was used to translate the raw electrical scan signals obtained into meaningful flow front location data. This data was then displayed graphically onto a PC screen using a specially developed BASIC-based software program. FIG. 2 illustrates the type of data display one may obtain using the sensing grid herein.

In this Example, the sensor gap (the spacing between perpendicular, non-intersecting grid lines) was approximately 0.25 inches +/−0.08 inches.

While particular embodiments of the present invention have been shown and described, it will be obvious to those skilled in the art that changes and modifications may be made without departing from this invention. Therefore, it is intended that the claims herein are to include all such obvious changes and modifications as fall within the true spirit and scope of this invention.

I claim:

1. A method for accurately monitoring the flow and cure rate of a resin material comprising
    pumping a resin material into a resistance monitoring device having electrically conductive sensor threads arranged in a non-intersecting, grid-like configuration so as to create a plurality of sensor gaps;
    allowing the pumped resin to advance through the grid-like configuration and sensor gaps of said resistance monitoring device;
    obtaining and sending an electrical signal received from said sensor gaps as the pumped resin reaches said sensor gaps to a signal interpreting apparatus and a data storage and presentation means; and
    interpreting the flow and cure rate of said resin material using said signal interpreting apparatus and said data storage and presentation means to interpret said electrical signal and display said interpretation, wherein the ends of said electrically conductive sensor threads serve as leads which are connected to said signal interpreting apparatus which in turn is connected to said data storage and presentation means.

2. A method in accordance with claim 1, wherein said signal interpreting apparatus is a scanner; and wherein said data storage and presentation means is a computer.

3. A method in accordance with claim 1, wherein the electrically conductive sensor threads are composed of graphite, lead, aluminum, copper, lead coated glass, metal oxides or electrically conductive polymeric materials.

4. A method in accordance with claim 1, wherein the electrically conductive sensor threads have a length of about 0.5 m to about 10 m; a diameter of about 0.2 cm to about 0.8 cm; and wherein the distance between adjacent, side-by-side parallel electrically conductive sensor threads is approximately 20 times that of the diameter of the sensor threads employed.

5. An apparatus for monitoring resin flow and its cure progress during a resin fabrication process, wherein said apparatus comprises
    a resin supply port;
    a resin mold containing therein a resistance, capacitance, electrical or dielectrical monitoring device having electrically conductive sensor threads arranged in a non-intersecting, grid-like configuration so as to create a plurality of sensor gaps;
    a signal interpreting apparatus; and
    a data storage and presentation means; wherein said resistance, capacitance, electrical or dielectrical monitoring device is present throughout said resin mold; and wherein said sensor threads are woven into or placed between successive layers of reinforcement materials to facilitate said non-intersecting, grid-like configuration.

6. An apparatus in accordance with claim 5, wherein said successive layer of reinforcement materials is woven roving glass.

7. An apparatus in accordance with claim 5, wherein the ends of said electrically conductive sensor threads serve as leads which are connected to said signal interpreting apparatus which in turn is connected to said data storage and presentation means.

8. An apparatus in accordance with claim 5, wherein said signal interpreting apparatus is a scanner; and wherein said data storage and presentation means is a computer.

9. An apparatus in accordance with claim 5, wherein the electrically conductive sensor threads are composed of graphite, lead, aluminum, copper, lead coated glass, metal, metal oxides, or electrically conductive polymeric materials.

10. An apparatus in accordance with claim 5, wherein the electrically conductive sensor threads have a length of about 0.5 m to about 10 m; a diameter of about 0.2 cm to about 0.8 cm; and wherein the distance between adjacent, side-by-side parallel electrically conductive sensor threads is approximately 20 times that of the diameter of the sensor threads employed.

11. An apparatus for monitoring resin flow and its cure progress during a resin fabrication process, wherein said apparatus comprises
    a resin supply port;
    a resin mold containing therein a resistance, capacitance, electrical or dielectrical monitoring device having electrically conductive sensor threads arranged in a non-intersecting, grid-like configuration so as to create a plurality of sensor gaps;
    a signal interpreting apparatus; and
    a data storage and presentation means; wherein said resistance, capacitance, electrical or dielectrical monitoring device is present throughout said resin mold; and wherein said sensor threads are connected to the perimeter of said resin mold to facilitate said non-intersecting, grid-like configuration.

12. An apparatus in accordance with claim 11, wherein the ends of said electrically conductive sensor threads serve as leads which are connected to said signal interpreting apparatus which in turn is connected to said data storage and presentation means.

13. An apparatus in accordance with claim 11, wherein said signal interpreting apparatus is a scanner; and wherein said data storage and presentation means is a computer.

14. An apparatus in accordance with claim 11, wherein the electrically conductive sensor threads are composed of graphite, lead, aluminum, copper, lead coated glass, metal, metal oxides, or electrically conductive polymeric materials.

15. An apparatus in accordance with claim 11, wherein the electrically conductive sensor threads have a length of about 0.5 m to about 10 m; a diameter of about 0.2 cm to about 0.8 cm; and wherein the distance between adjacent, side-by-side parallel electrically conductive sensor threads is approximately 20 times that of the diameter of the sensor threads employed.

* * * * *